(12) United States Patent
Belluche et al.

(10) Patent No.: US 7,828,832 B2
(45) Date of Patent: Nov. 9, 2010

(54) INTRAVASCULAR DEPLOYMENT DEVICE WITH IMPROVED DEPLOYMENT CAPABILITY

(75) Inventors: Terrance D. Belluche, North Hampton, NH (US); Scott Doig, Santa Rosa, CA (US); Hillary K. Huszar, San Francisco, CA (US); Andrew Kim, San Francisco, CA (US); Stephen Clark Meier, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 706 days.

(21) Appl. No.: 11/108,613

(22) Filed: Apr. 18, 2005

(65) Prior Publication Data

US 2006/0235502 A1    Oct. 19, 2006

(51) Int. Cl.
A61F 2/06 (2006.01)
(52) U.S. Cl. ..................................... 623/1.11
(58) Field of Classification Search ................ 623/1.11; 604/523–526
See application file for complete search history.

(56) References Cited

U.S. PATENT DOCUMENTS

| | | | |
|---|---|---|---|
| 3,844,137 A | 10/1974 | Zugel | |
| 4,921,482 A | 5/1990 | Hammerslag et al. | |
| 4,998,923 A | 3/1991 | Samson et al. | |
| 5,069,674 A | 12/1991 | Fearnot et al. | |
| 5,095,915 A | 3/1992 | Engelson | |
| 5,107,852 A | 4/1992 | Davidson et al. | |
| 5,125,909 A * | 6/1992 | Heimberger | 604/264 |
| 5,308,342 A * | 5/1994 | Sepetka et al. | 604/525 |
| 5,322,064 A | 6/1994 | Lundquist | |
| 5,573,520 A | 11/1996 | Schwartz et al. | |
| 5,695,483 A | 12/1997 | Samson et al. | |
| 5,743,876 A | 4/1998 | Swanson | |
| 5,897,537 A | 4/1999 | Berg et al. | |
| 5,916,177 A | 6/1999 | Schwager | |
| 6,004,279 A | 12/1999 | Crowley et al. | |
| 6,027,863 A * | 2/2000 | Donadio, III | 430/320 |
| 6,107,004 A | 8/2000 | Donadio, III | |
| 6,117,140 A * | 9/2000 | Munsinger | 606/108 |
| 6,183,424 B1 | 2/2001 | Schwager | |

(Continued)

FOREIGN PATENT DOCUMENTS

EP    1040843    10/2000

(Continued)

*Primary Examiner*—(Jackie) Tan-Uyen T Ho
*Assistant Examiner*—Gregory Anderson

(57) ABSTRACT

An intravascular delivery catheter includes a middle member or manipulator to ameliorate the effect of buckling of the graft cover during the tracking or positioning of the delivery device within a body flow lumen to deploy an exclusion device, such a stent graft. The delivery device/catheter includes a region or regions of lower resistance to bending than other portions of the delivery device, which are positioned, within the delivery device, to preferentially bend the delivery system at locations where buckling will have minimal effect upon the deployment of the exclusion device from the delivery system. The preferential bending is accomplished, by providing a middle member/manipulator that is a rod with laterally oriented slots, having different depth and spacing configurations, or by using a wire coil as a portion of the middle member where the variable stiffness is created either by providing a variable/ multiple coil diameter or by using a wire having a variable diameter along its length while the wire coil diameter is relatively uniform.

4 Claims, 12 Drawing Sheets

U.S. PATENT DOCUMENTS

| | | |
|---|---|---|
| 6,273,876 B1 | 8/2001 | Klima et al. |
| 6,500,130 B2 | 12/2002 | Kinsella et al. |
| 6,579,246 B2 | 6/2003 | Jacobsen et al. |
| 6,604,003 B2 | 8/2003 | Fredricks et al. |
| 6,652,508 B2 | 11/2003 | Griffin et al. |
| 6,716,207 B2 | 4/2004 | Farnholtz |
| 6,776,765 B2 | 8/2004 | Soukup et al. |

FOREIGN PATENT DOCUMENTS

| | | |
|---|---|---|
| EP | 1208816 | 5/2002 |
| WO | WO 93/04722 | 3/1993 |
| WO | WO 98/52636 | 11/1998 |

* cited by examiner

INTRAVASCULAR DEPLOYMENT DEVICE WITH IMPROVED DEPLOYMENT CAPABILITY

BACKGROUND OF THE INVENTION

1. Field of the Invention

The present invention relates to the field of intravascular deployment systems. More particularly, the invention relates to the field of apparatus and methods for the deployment of intravascular devices, including exclusion devices such as stent grafts, where interference between the components of the delivery apparatus may lead to an inability to deploy the device or result in partial deployment of the device.

2. Background of the Art

Intravascular deployment of exclusion devices (stent grafts) is a methodology used to deliver an exclusion device to a portion of a body flow lumen that is diseased or damaged, such as an aneurysmal portion of an aorta, and, thence deploy the exclusion device to span the diseased or damaged portion of the aorta and thereby provide a synthetic flow conduit which passes through the diseased or damaged portion of the aorta and seals against healthy tissue of the aorta at locations upstream and downstream of the diseased or damaged portion thereof. By deploying the exclusion device intravascularly, the diseased or damaged portion of the flow lumen may be bypassed with the exclusion device forming a synthetic flow lumen, without the need to remove the diseased or damaged portion of the flow lumen, which would require far more invasive surgery. Where the diseased or damaged flow lumen is the aorta, either the abdominal aorta or thoracic aorta, the use of intravascular deployment of a stent graft to exclude the diseased or damaged portion of the aorta, and provide a secondary flow conduit within the aorta, is well known to those skilled in the art.

A stent graft includes a stent portion or frame, which is in some embodiments configured as a plurality of wires formed into hoops, to which is affixed a graft material, which is likewise formed into a hoop shape to provide a synthetic flow conduit for blood once the stent graft is deployed in the aorta. The stent graft is sized to have a length sufficient to span the diseased or damaged portion of the aorta, and overlap 10 to 25 mm onto the adjacent healthy tissue and a diameter one of two millimeters larger than the diameter of the healthy portion of the aorta located on the upstream and downstream ends, in a blood flow direction perspective, of the diseased or damaged portion of the aorta, such that the stent portion biases the graft material against healthy aorta wall tissue at the upstream and downstream ends of the stent graft to seal off the disease or damaged aorta wall from further blood flow thereto at systemic pressure.

To enable intravascular deployment of the stent graft, the stent graft is first radially compressed to a small diameter, on the order of a centimeter or less, and loaded into a tubular element, specifically a graft cover portion of a deployment system. The deployment system, includes the tubular graft cover, within which the compressed stent graft is inserted at the distal end thereof, a manipulator or middle member within the stent graft extends through the graft cover to the proximal end, thereof, and a guidewire can, extend through a bore in the middle member which extends the length of middle member and through the compressed stent graft, such that a first end of the guidewire can be disposed beyond the proximal end of the graft cover, and a second end is extendable from the bore at the distal end of the graft cover. The middle member serves several purposes: It provides the bore through which the guidewire is received such that the middle member, and the graft cover and stent graft thereover; may be tracked over the guidewire; it provides a support or "stent stop" against which the stent graft will bear during the deployment of the stent graft procedure; during the procedure the graft cover is retracted from around the stent graft and middle member; and, it provides, in conjunction with the graft cover, support or structure to carry the axial, rotational and bending loads imposed upon the delivery system as it is tracked over the guidewire.

Endovascular delivery of a stent graft is commonly facilitated by opening an incision into one of the iliac arteries adjacent the groin of the patient, and first deploying the guidewire, having fluoroscopic markers adjacent the distal or deployed, end thereof, through or along the artery to a position wherein the distal end of the guidewire extends beyond the diseased portion of the aorta. The stent graft delivery catheter having the graft cover, having the middle member and the stent graft held therein, is then tracked along the guidewire, such that the distal end of the graft cover is positioned upstream of the deployment location of the stent graft. The distal end of the graft cover is then exposed to the aorta, and the graft cover is retracted while the middle member is held stationary, such that the stent graft cannot move relative to the stationary stent stop and the stent graft becomes exposed to the aorta and is deployed from the graft cover.

One issue which may arise during deployment of the stent graft from the graft cover, and which has serious consequences, is that the graft cover may become bound up with the stent stop, such that the graft cover cannot be retracted or moved relative to the stent stop. One cause of this binding is buckling of the graft cover, which can occur when the graft cover and middle member are being tracked along the guidewire through regions of tortuous anatomy. Because the graft cover is a thin walled tubular column, which is being pushed through restricted or tortuous pathways of an artery to reach the diseased portion of the aorta, forces may be imposed axially, i.e., the pushing of the graft cover from its proximal end as it is being tracked over the guidewire, rotationally, by forces imposed on the graft cover as the surgeon or other practitioner rotates the proximal end of the graft cover to properly align the stent graft at the deployment location, and in bending, by forces which are imposed as the delivery system is tracked through turns or restrictions in the introduction artery or the aorta. Turns result in the delivery system having one portion of the delivery system positioned in a generally linear path which is at an angle to the immediately adjacent portions of the delivery catheter. If the sum of these forces or loads exceeds the buckling strength or capacity of the graft cover, i.e., its resistance to excess deformation, then the graft cover can buckle. When such buckling occurs, the span across the interior of the graft cover is reduced at the buckle. If this occurs in the region of the graft cover extending about the stent graft held within the graft cover, as the graft cover is retracted to deploy the stent graft, the cover can become bound against (create an interference fit with) the enlarged portion of the middle member which forms the stent stop, preventing further retraction of the graft cover. Where the buckle interferes with the stent stop before substantial deployment of the stent graft, this is an inconvenience, as the procedure must be terminated and the delivery system with the stent graft intact, must be removed from the body by reverse tracking thereof over the guidewire. Where the buckle is brought against the stent stop after a portion of the stent graft is deployed, and the surgeon cannot pull the graft cover further over the middle member, immediate emergency surgery, to open the patient through the chest and invasively repair the situation is warranted.

SUMMARY OF THE INVENTION

A delivery system for an exclusion device is provided which includes: a tubular delivery portion, within which a device to be intravascularly deployed is releasably held, and a manipulator, extendable along the hollow, tubular interior of the tubular delivery portion which includes a variable stiffness, (or resistance to bending portion), disposable immediately adjacent to the portion of the tubular delivery portion within which the device to be deployed is held. In one aspect, the delivery system includes guidewire, a middle member providing the manipulator and which is disposable over the guidewire and trackable thereover, and a graft cover providing the tubular delivery portion, disposable over the middle member and trackable over the guidewire therewith, wherein the variable stiffness member is positioned adjacent to the position of the exclusion device held in the graft cover prior to the deployment of the exclusion device.

In one aspect the variable stiffness member is a generally longitudinal member having a length and a cross section or diameter which forms a portion of, or a replaces a portion of, the middle member. This variable stiffness member may include a large diameter portion thereof having a diameter different than the diameter of the remainder thereof, a uniform diameter portion having a uniform diameter having regions of different stiffness thereof, or may be formed by winding a material having uniform or variable stiffness inherent in the material, and selectively providing a coil diameter to result in a variable stiffness of the resulting coil along its length. In an additional aspect, the variable stiffness member may have a generally uniform first cross section, with at least two regions of different stiffness formed by having a variable second cross section thereof. The variable stiffness member may also comprise a relatively uniform diameter, rod-like member, having formed therewith regions of different stiffness. In one aspect, this variable stiffness is provided by forming the rod-like member of material having different durometer hardness. In another aspect, this variable stiffness is provided by providing slots across the rod, transverse to its length, which have a varying depth and/or width.

Where the variable stiffness member forms a part of, or replaces a portion of, the middle member, the location of lowest stiffness, e.g., of the greatest flexibility, may be selectively positioned with respect to the stent stop. Thus, in one aspect, the portion of the variable stiffness member closest to the stent stop has the lowest stiffness of any region of the variable stiffness member. In another aspect, the lowest stiffness portion may be positioned intermediate of portions of greater stiffness, or furthest from the stent stop.

In another aspect, the variable stiffness member includes at least a low stiffness portion having a stiffness which is less stiff, or less resistant to bending, than is the compressed stent graft held in the graft cover. As a result, when the stent graft is being introduced over the guidewire through tortuous anatomy, buckling will more likely occur at the location of greatest bending or flexing of the graft cover, which location will occur along a least stiff portion of the stent graft/variable stiffness member combination, which is located at the proximal end of the stent stop and thus in a location where the buckle in the graft cover will not create an interference fit with the stent stop and thereby prevent retraction of the graft cover.

In another aspect, runners, having a generally planar profile, extend from the stent stop over the stent graft held within the graft cover, and terminate prior to reaching the full length of the stent graft within the graft cover. In one aspect, the runners include a proximal portion affixed over an outer circumferential wall of a stent stop and extending therefrom partially over the stent graft held in the graft cover. Upon deployment of the stent graft, the runners provide a bearing surface over which a collapsed or buckled portion of the graft cover may slide and help maintain the diameter of the graft cover over the stent stop to prevent binding therewith.

DESCRIPTION OF THE EMBODIMENTS

Method and apparatus are provided for the delivery of exclusion devices, such as stent grafts, to aneurysmal sites in a patient, wherein the effect of buckling of the outer tubular sheath, or graft cover, of the delivery device, on the ability to deploy the stent graft therefrom is mitigated.

Figure 1:
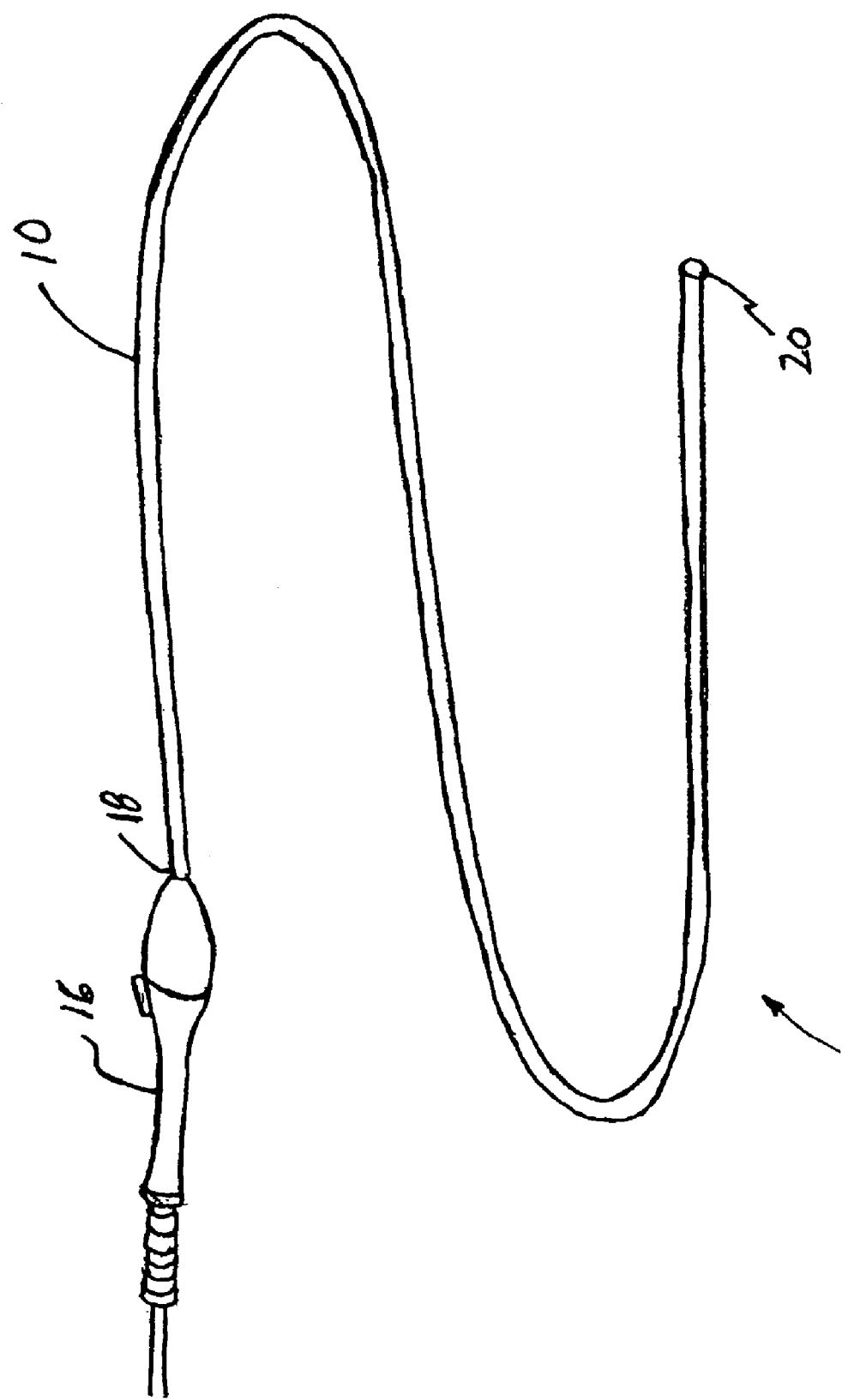
FIG. 1 is a schematic perspective view of a delivery system according to the present invention.

Referring initially to FIG. 1, there is shown a delivery system 10 according to the present invention, which generally includes: a tubular delivery catheter 14, terminating at a distal end 20; an operator 16, disposed adjacent to proximal end 18 of tubular delivery catheter 14 and positioned to enable a surgeon or technician to manipulate the tubular delivery catheter 14 within a flow lumen (not shown) of a patient. Thus, in use, the tubular delivery catheter is tracked in an artery (not shown) of a patient, to position the distal end 20 thereof at a position, in a blood flow direction, upstream of the aneurysm (not shown), wherein an exclusion device may be deployed across the aneurysmal site. Operator 16 is shown and described in U.S. published Patent Application No. 2003/0199966, which is incorporated herein by reference.

Figure 2:
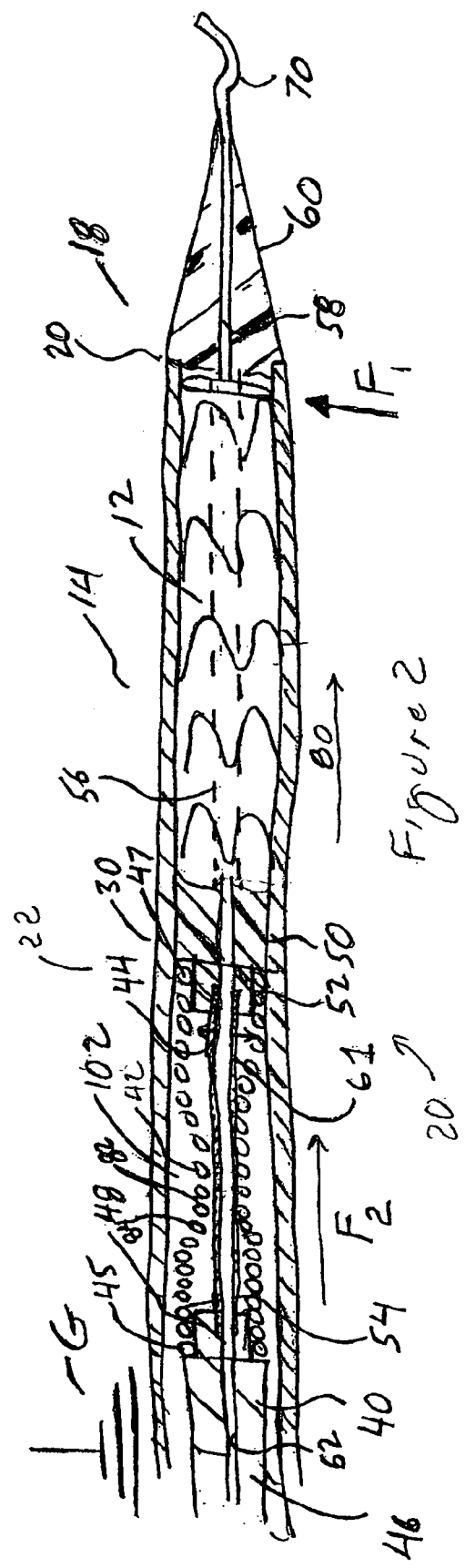
FIG. 2 is a partial, cross sectional view, of a portion of the delivery system of FIG. 1.

Referring now to FIG. 2, the position of the tubular delivery catheter 14 adjacent to distal end 20 of the delivery system 14 is shown in cross section, disclosing the internal features thereof. Tubular delivery catheter 14 generally includes an outer tubular graft cover 30, which is a generally thin walled tube within which is held, at a position immediately proximal to the distal end 20, a stent graft 12 for deployment across an aneurysmal site in a patient's aorta. Additionally, a middle member 40 is provided, which extends from a position, prior to deployment of the stent graft 12 from the tubular delivery catheter 14, that is immediately proximal to the stent graft 12, i.e., further proximal than the position of stent graft 12, and extends therefrom to proximal end 18 of the catheter 10 where it extends beyond the graft cover 30 and on into the operator 16. By retracting the graft cover 30 over the middle member 40, for example by moving the graft cover 30 proximally while using the operator 16 to hold the middle member 40 stationary, the stent graft 12 will be held in position as it contacts and is blocked by a stop 50 near the distal end of the middle member 40 as the graft cover 30 retracts over the stent graft 12, ultimately releasing the stent graft 12 from the graft cover 30.

Referring still to FIG. 2, middle member 40 includes a first portion 46, which is a generally cylindrical rod shaped flexible member which extends from the proximal end 18 of the graft cover 30 to a position adjacent to, but spaced from, the proximal end (relative to the catheter) of the stent graft 12 within the graft cover 30, where the first portion 46 terminates in a threaded extending boss 48. Middle member 40 further includes the stent stop 50 located immediately adjacent the proximal end of stent graft 12 in graft cover 30, and which likewise includes a threaded boss 52 which is positioned to face boss 48, such that a variable stiffness member, in this case a variable stiffness coil 54 extends between, and is threadingly secured to threaded bosses 48, 52 to secure the stent stop 50 to the first portion 46 of the middle member 40. Stent stop 50 further includes a tubular extension 56 (shown with dashed lines), preferably integrally formed therewith, which extends from the proximal end, i.e., stent graft 12 engaging side, of the stent stop 50 and terminates adjacent to distal end 20 where it is attached to tapered introduction portion (tip) 60. A first wire bore 58 extends centrally through the stent stop 50, tubular extension 56 and tapered introduction portion 60, and a second wire bore 62 extends the length of first portion 46 of middle member 40. A guidewire guide tube 61 extends between the first wire bore 58 to the second wire bore 62, to guide the passage of a guidewire in the space between the bores so that no threading of the bore is needed. A guidewire 70 is extendible through bores 58, 62, such that the tubular delivery catheter may be tracked over the guidewire 70 to position the delivery catheter 14 for the deployment of the stent graft 12.

Figure 3:
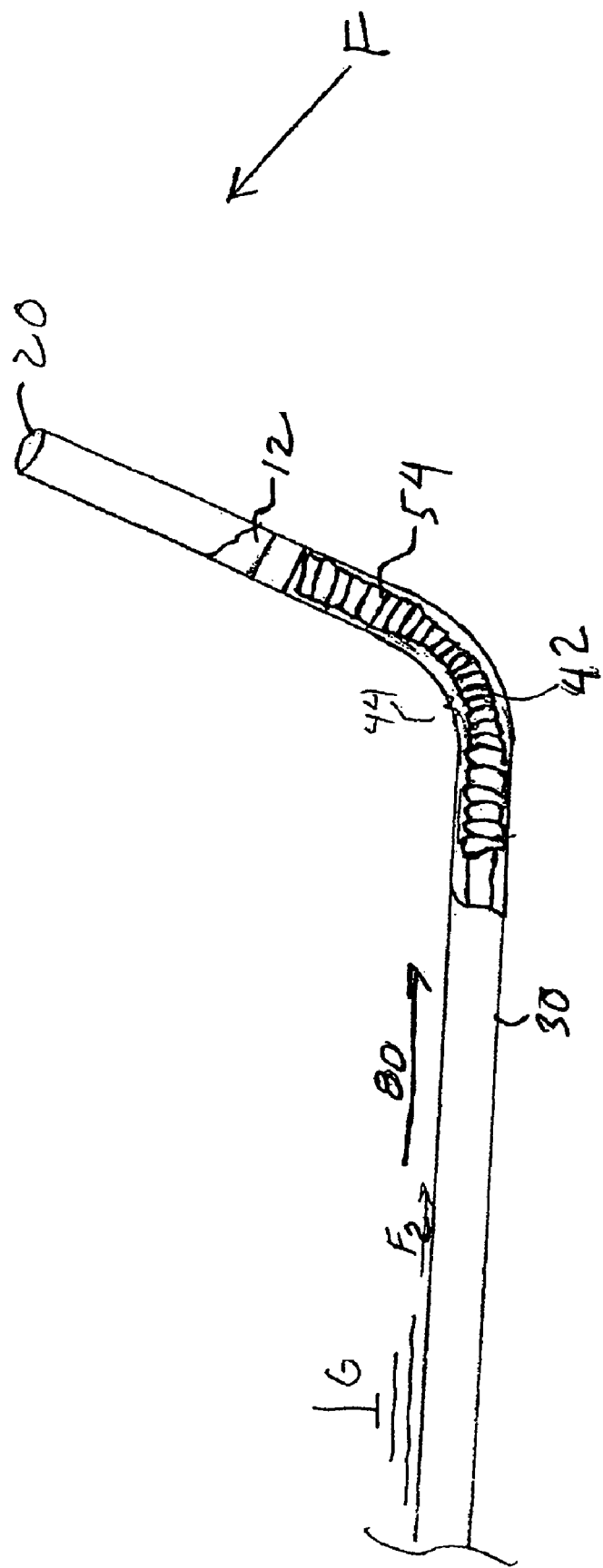
FIG. 3 is a partial side view, partially in cut-away, of the delivery system of FIGS. 1 and 2, showing the selective bending location provided by the locating of a variable stiffness middle member within the delivery system.

The variable stiffness coil 54 is, in this embodiment, specifically configured to provide a structurally weaker portion, with respect to resistance to bending of both the stent graft 12 as loaded into the graft cover 30 and the remainder of the middle member 40, at a location immediately proximal to the position of the stent graft 12 with in graft cover 20. This lower stiffness portion 42 of variable stiffness coil 54 is so positioned, such that upon application of a force $F_1$ adjacent to distal end 20, while the graft cover 30 is grounded against anatomy at G, (or vice-versa) bending of the graft cover 30 will occur primarily and preferentially at the lower stiffness portion 42 as shown in FIG. 3. Thus, where an axial force $F_2$ is applied linearly along the length of the tubular delivery catheter 14, in combination with the bending force $F_1$, exceeds the strength of the tubular delivery sheath 20 against buckling, the area of highest stress or load will occur where the graft cover 30 is bending the most, in this case about the position of the lower stiffness portion 42, and thus buckle 44 will occur with portions of the catheter wall extending inwardly.

To provide, in this embodiment, the lower stiffness portion 42, the variable stiffness coil 54 is configured of a wire, such as stainless steel wire, having a wire diameter of approximately 0.05 to 0.10 inches, which is wound into a coil shape as shown in FIG. 2, such that the coil diameter 44 at the opposed ends 45, 47 of the coil 54 is larger than the coil diameter 44 at the lower stiffness portion 42. Thus, if the proximal end 45 of coil 54 is held relatively stationary, and the distal end 47 of the coil 54 is located in threaded engagement with stent stop 50 is caused to be loaded in a direction generally perpendicular to the axial configuration of the delivery catheter 14 as shown by G and $F_1$ in FIG. 2, lower stiffness portion 42, having the lowest resistance to a bending moment of the several different continuous portions of the coil 54, will bend in an arc about the lower stiffness portion 42 such that the remaining portions of the coil 54 remain aligned in a relatively straight or linear configuration. Additionally, by lower stiffness portion 42 having a lower resistance to bending than any other portion of the middle member 40 or the loaded stent graft 12, localized bending of the delivery catheter 10 in the region of the graft cover 30 within which the stent graft 12 is held and the portions of the middle portion 40 adjacent to the stent graft 12 within graft cover 30 will occur at lower stiffness portion 42. As the region of greatest load on the graft cover 30 will occur where the axial, torsional and bending loads are maximum, the forced bending of the delivery catheter 14 at the lower stiffness portion 42 will tend to create the maximum buckling stress on the inside radius of the bent graft cover 30 at that location (the stress contributing to buckling imposed by bending outweighs the contribution attributable to axial or torsional loading). A concentration of bending forces on the portion of the graft cover 30 over the stent graft 12 occurs immediately adjacent to that portion of the graft cover 30 overlying the lower stiffness portion 42 as contribution of the axial and rotational loading or forces, are considered uniform along the length of the graft cover 30. Buckling and thus potential for kinking and binding of the graft cover 30 as is retracted over the stent stop 50 is eliminated, as the buckling is now caused to preferentially occur at a location on the inside radius of the bent graft cover 30 proximal to the stent stop 50 adjacent to the lower stiffness portion 42 of the middle member.

In addition to providing a specific location for the initiation and maintenance of buckling, the variable stiffness member also provides the capability to carry both axial and rotational loads, so as to assist in the tracking of the delivery catheter 14 over the guidewire 70. Specifically, as the delivery catheter 14 is tracked along the guidewire 70, the surgeon or other person guiding the delivery catheter 14 will provide a pushing force along the axial direction 80 of the delivery catheter 70, including the graft cover 30 and the middle member 40, which force is necessary at a low level to simply track the delivery catheter 14 over the guidewire 70, and a greater axial force may need to be provided in the direction 80 where the delivery catheter encounters restricted or tortuous anatomy. If the middle member 40 did not carry a or support a portion of this axial force, and the entire force were carried or distributed over the cross section of the graft cover 30, the graft cover would be much more likely to buckle. The middle member first portion 46 thus supports a portion of this load or force, and the variable stiffness portion 42 must also be capable of supporting this load without significant distortion thereof. This is accomplished by the combination of the flanks 82 of the spring windings 84 (being one continuous length of wire which, in this embodiment is wound at a variable coil diameter) contacting each other and thus providing frictional resistance to relative movement therebetween, as well as by the actual spring force of the variable stiffness coil 54 itself being resistant to further expansion or contraction of the coil diameter 44. Additionally, rotational loads, such as when the surgeon needs to rotate the delivery catheter to properly position radiological markings for proper positioning of the stent graft 12 for deployment, or for aligning branch vessel openings of the stent graft with the deployment location flow lumen anatomy, must be supported at least in part by the middle member 40 so as to not overload the graft cover 30 which would induce buckling thereof. A coil structure such as the variable stiffness member 42 provides rotational support in two rotational directions, i.e., clockwise and counter-clockwise. The ends of the ends of the variable stiffness portion 42 are glued or otherwise fixedly attached to the bosses on which they are threaded. Where the rotation of the middle member is in the direction of the windings 86 of the coil, the coil will have substantial resistance to further internal turning, i.e., further torsional winding thereof, simply due to the small diameter thereof. Additionally, where the rotational load is provided in the direction against the direction of winding, the spring force of the variable stiffness coil 54 will tend to oppose unwinding thereof to any substantial degree. Thus, the variable stiffness member as provided by the variable stiffness coil 54 is capable of supporting axial and rotational loads during the tracking of the delivery catheter 14 over the guidewire 70, but will provide a relatively low resistance to bending moment caused by tortuous anatomy, and thus enable buckling of the inside radius of the graft cover 30 to preferentially occur over the region of the variable stiffness coil during stent graft 12 deployment, and thus significantly reduce the likelihood that buckling will occur in the wall of the graft cover 30 in the region thereof overlying the stent graft 12 deployed therein, which could interfere with the ability to retract the graft cover 42 if the buckle or kink in the graft cover pinches against, and thereby locks against, the stent stop 50.

Figure 4:
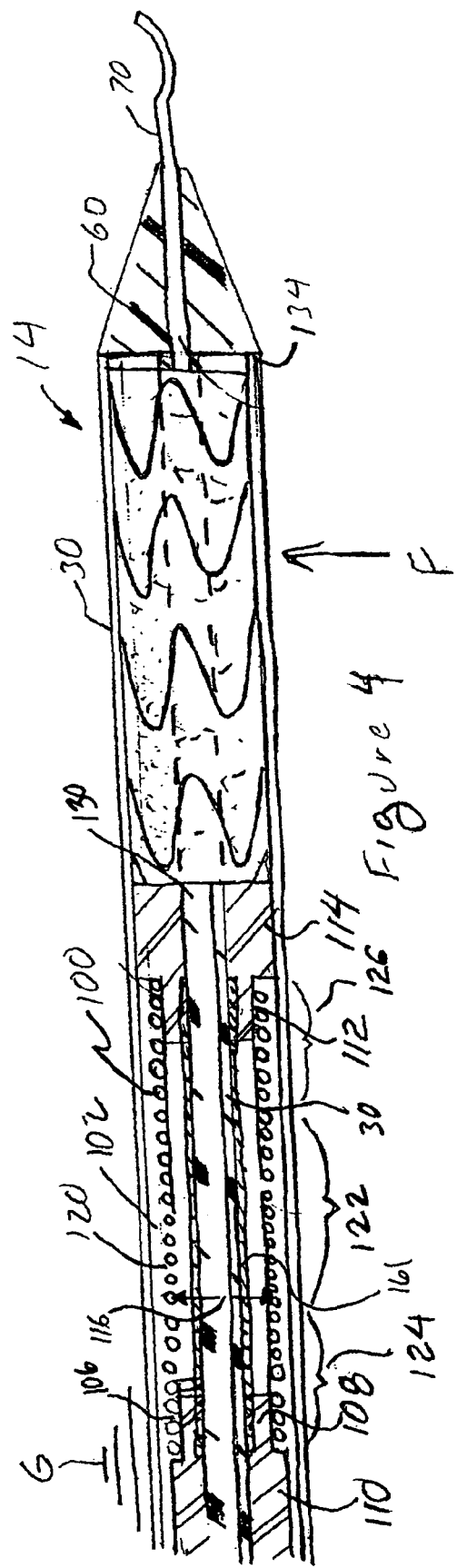
FIG. 4 is a partial cross sectional view of an alternative embodiment of a portion of a delivery system of FIG. 1.

Referring now to FIG. 4, there is shown an alternative embodiment of the variable stiffness member of a delivery catheter 14, wherein a wire 100, having a variable wire diameter, is wound into a coil 102 for spanning and engaging deployment between a threaded boss 106 provided at the termination of the first portion 108 of a middle member 110, as in the embodiment shown and described with respect to FIG. 2, and the threaded boss 112 of a stent stop 114 as was shown and described with respect to FIG. 2. In this embodiment, the coil 102 is formed at a constant coil diameter 116, but a variation in the diameter of the wire 100 results in a fixed diameter coil having a lower stiffness portion 120 thereof, where the smaller diameter of the wire 100 is present, as compared to where the coil comprises a larger diameter portions of the wire 100. In this embodiment, the coil 104 is configured to include a central portion 122 of lower stiffness to bending than first coil portion 124 and second coil portion 126 disposed, linearly, to either side of central portion 122. Thus, when lateral forces are applied against the component of the delivery catheter 14 to either (as measured linearly) side of the coil 104, such as via load $F_1$ and grounded location G as shown in FIG. 3, the coil 104, as opposed to the middle member 110 or the stent graft 12 will tend to bend, at the central portion 122 wherein the lowest stiffness portion 120 is located, and thus if the total compressive forces on the graft cover 30, in combination with the forces caused by bending of the graft cover 30, exceed the compressive strength of the graft cover, the graft cover will buckle, but will do so in a location circumferentially adjacent to the coil 104, and thus not in a location where the buckle would prevent retraction of the graft cover past the stent stop 114.

Referring again to FIG. 4, an alternative construction of the middle member, as compared to that shown and described with respect to FIG. 2, is shown, wherein in this case, a tapered introduction portion 60' is provided which may be moved, axially, i.e., along the direction of the length of the graft cover 30, after tracking of the delivery system 14 to the aneurysmal site, but before the initiation of relative movement of the graft cover 30 over the middle member 40, to provide additional space between the front of the stent graft 12 held in the graft cover 30 and the tapered introduction portion 60' during deployment of the stent graft 12 into an aneurismal site. To provide this capability, an internal secondary tube 130 surrounds the guide wire 70, and this secondary tube 130 connects to and forms an integral extension of the tapered introduction portion 60. This secondary tube 130 extends, through the entire length (tube 130 shown in dashed lines through stent graft 12) of the graft cover 30, through a bore in both the stent stop 114 and the middle member 110, and out the proximal end (FIG. 1) of the delivery system. By pushing the secondary tube 130 from the proximal end of the catheter 14 distally, the tapered introduction portion 60 is moved distally from the end 134 of the graft cover 30, and thus creates a gap between the proximal end of the tapered introduction portion 60 and the graft cover 30.

Although the coil 54 has been described in terms of having a variable coil diameter of constant wire diameter, and the coil 102 has been described in terms of a constant diameter coil wound from wire having a variable diameter, it is specifically contemplated that a variable flexible element may be provided by winding a coil of variable coil diameter and variable wire diameter, such that the region of the coil having the smallest coil diameter also has the smallest wire diameter. Thus, the region of greatest flexibility is also the region of the smallest diameter. Additionally, although the region of the greatest flexibility of the coil has been shown and described as the central portion of a linear coil, the area of the coil having the region of greatest flexibility may also be located closest to, or furthest from, the stent stop 50, 114, by providing that the region of smallest coil diameter, area of smallest wire diameter, or the combination of smallest coil and smallest wire diameter, be closest or furthest from the stent stop 50, 114 on the coil. Preferably, the region of the coil having the greatest flexibility, or least resistance to bending, is located closest to the first portion of the middle member, e.g., furthest from the stent stop 50, 114. Finally, the coil may be provided as a non-variable stiffness element, but as an element having significantly less resistance to bending than the stent graft or the middle member. In such a configuration, a coil of continuous cross section and continuous, i.e., equal wire diameter is provided. As the stiffness of the coil is selected, by trial and error, to be less than that of the stent graft, the coil will bend in preference over the stent graft, thus helping to create conditions on the graft cover which, if the wall of graft cover is to buckle, will cause it to buckle over the coil.

Figure 5:
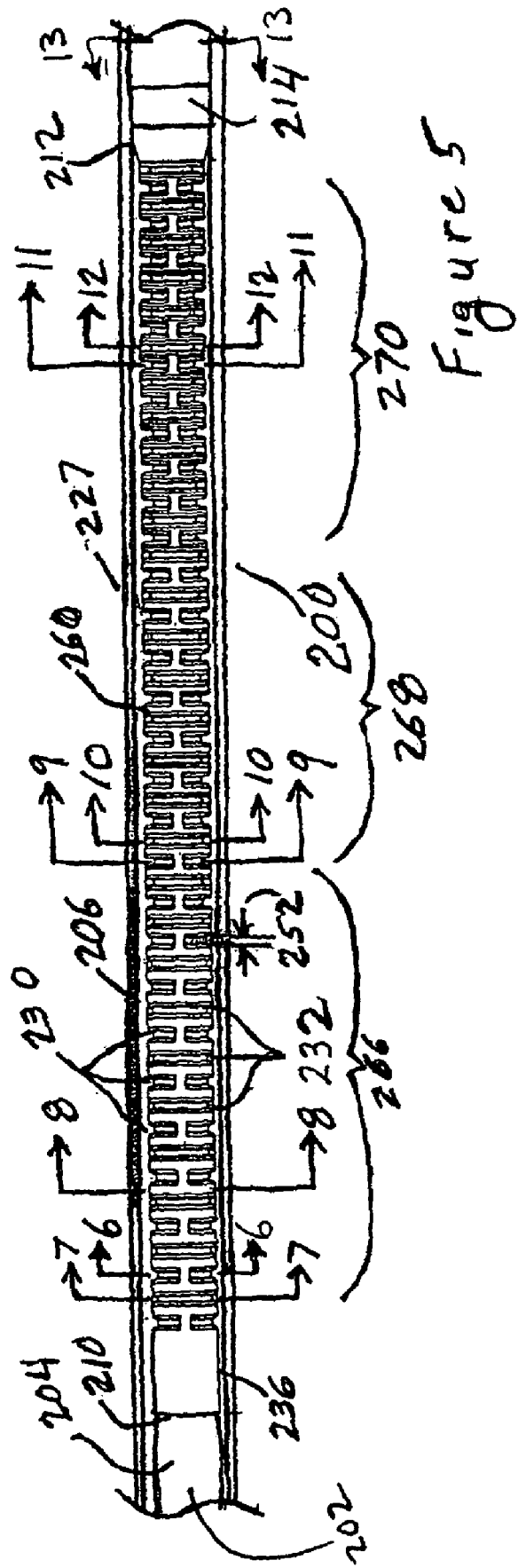
FIG. 5 shows a catheter cut away to show a plan view of an alternative embodiment of a variable stiffness member.
Figure 13:
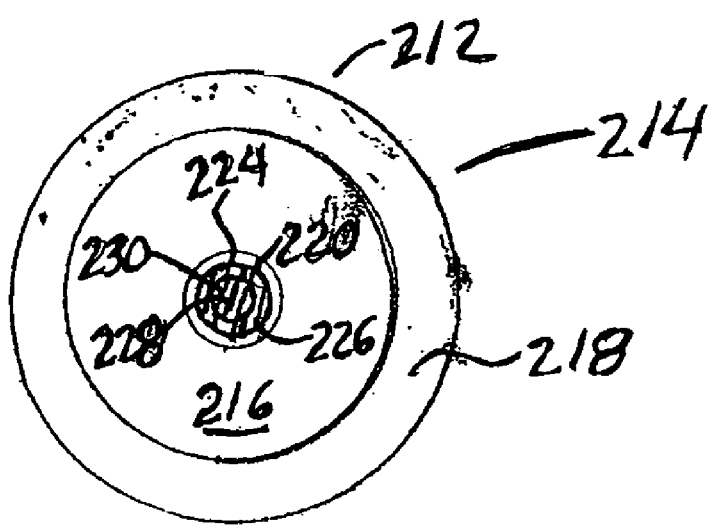
FIG. 13 is a cross sectional view of the variable stiffness member of FIG. 5 at 13-13.

Referring now to FIG. 5, an additional embodiment of the variable stiffness member is shown, wherein a rod 200, preferably formed of a biocompatible polymer such as Vestamid or Pemax, is provided to form the proximal end 202 of the middle member 204 of this embodiment. The rod 200 in this embodiment includes a generally constant thickness outer portion 206 which extends substantially its entire length terminating in opposed ends 210, 212. End 210 is integrally formed with middle member 204, or alternatively, can be affixed to the middle member by adhesive or other methodologies for providing a secure connection therebetween. Referring briefly to FIG. 13, end 212 includes an enlarged diameter portion, extending over a relatively small, as compared to the overall length of the rod 200 to form an enlarged stent stop 214. The enlarged stent stop 214 includes a front or stent graft engaging face 216, from which, about its circumference, extends a frustroconical alignment lip 218 and about the center of face 216 extends a tapered tube 220 which extends therefrom to a position immediately adjacent to the back face of a tapered introduction portion (as shown as tapered introduction portion 60 in FIG. 2). A through bore 224 extends through the tapered tube, the variable stiffness rod 200 and the middle member 204, such that an hollow tubular introduction portion actuator tube 226 may extend from a position connected to a tapered introduction portion (as in FIG. 3) to a position exterior of the proximal end (not shown) of the delivery system for the movement of the introduction portion relative to the graft cover 227 is provided. A guidewire bore 228, through which a guidewire 230 may be extended, runs the entire length of the actuator tube 226.

Figure 6:
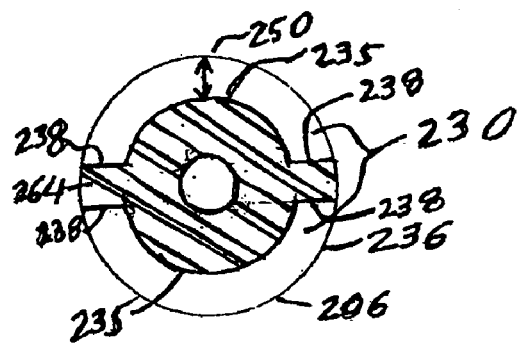
FIG. 6 is a cross sectional view of the variable stiffness member of FIG. 5 at 6-6.
Figure 7:
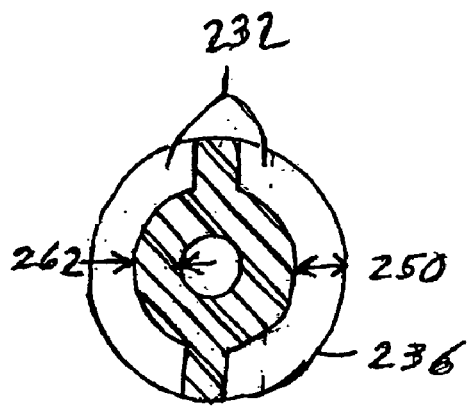
FIG. 7 is a cross sectional view of the variable stiffness member of FIG. 5 at 7-7.

Referring now to FIG. 6, rod 200 includes the aforementioned relatively constant thickness outer portion 206, and a second, variable thickness portion which, in this embodiment, includes a plurality of opposed offset slots 230, 232, such that a plurality of opposed slots extend inwardly of the rod from the outer surface 236 of the rod 200. Each of the slots 230, 232 is of a generally crescent shape, having an outer boundary defined by the radius of the relatively constant thickness outer portion 206 and an inner boundary defined by a partial circumferential wall 235 and opposed base 238, each of the bases 238 of each slot lying generally co-planer with one another. Additionally, for each of slots 230, a slot 232, having the same configuration, but offset, about the central longitudinal axis of the rod 200, by 90 degrees from slot 230. Thus, as is shown in FIG. 7, slot 232 includes the same partial circumferential wall 235 and co-planer bases 236 as were provided for slot 230 in FIG. 6. Slots 230, 232 also include a depth, as defined from the apex of partial-circumferential portion 235 to the closest portion of outer portion 206, and a width 252 (FIG. 5) Additionally, ribs 260 are provided between each adjacent slot 230, 232, and the body of the rod 200 between the partial circumferential portion 235 of each slot 230, 232 and the inner bore of the rod 200 forms a cylindrical wall 232, and the portion of the rod 200 between the adjacent bases 238 of opposed slots 230 or slots 232 forms a web 264.

Figure 8:
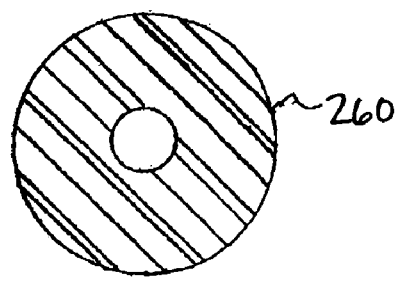
FIG. 8 is a cross sectional view of the variable stiffness member of FIG. 5 at 8-8.
Figure 9:
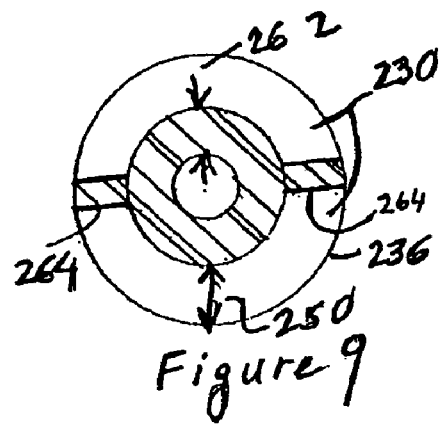
FIG. 9 is a cross sectional view of the variable stiffness member of FIG. 5 at 9-9.
Figure 10:
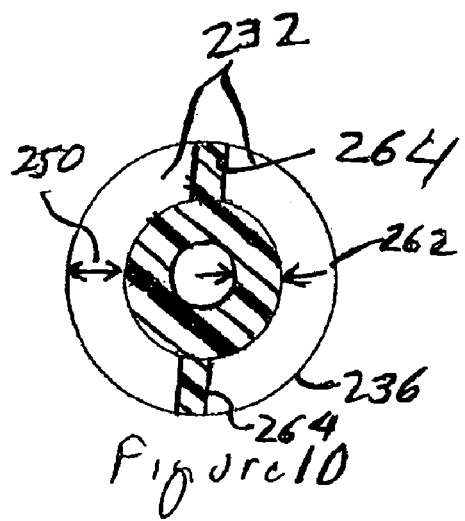
FIG. 10 is a cross sectional view of the variable stiffness member of FIG. 5 at 10-10.
Figure 11:
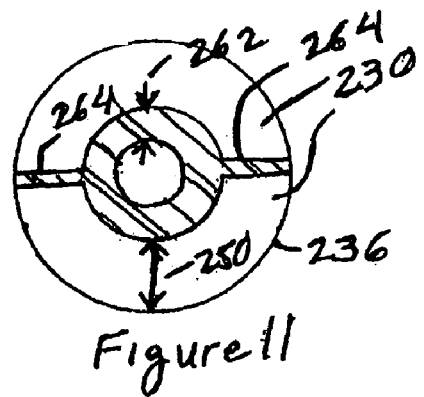
FIG. 11 is a cross sectional view of the variable stiffness member of FIG. 5 at 11-11.
Figure 12:
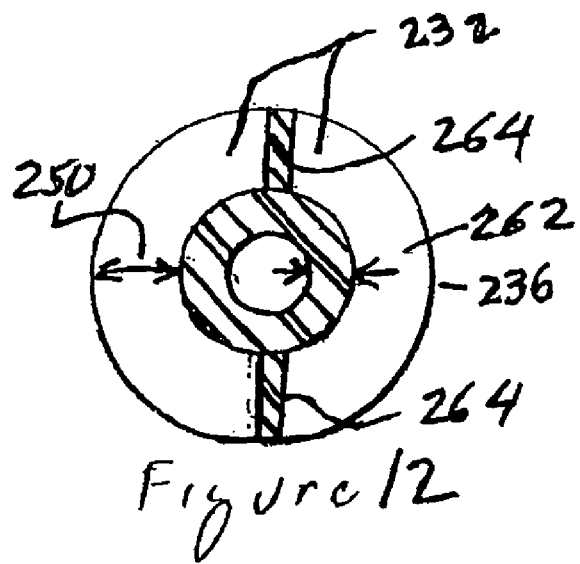
FIG. 12 is a cross sectional view of the variable stiffness member of FIG. 5 at 12-12.

Referring again to FIG. 5, the rod 200 includes three regions wherein adjacent slots are composed of generally equal depth and equally wide (as measured by the space between adjacent slots 230, 232) width, that depth and rib width being different in this construction in each of the three regions, but the slot width 252 remaining relatively constant. Thus a first region 266 of slots 230, 232 is composed of slots having only a first depth 250 are provided in the first portion 266, a second region of slots 268 composed of slots having only a second depth 250" deeper than the first depth, and a third region 270 of slots having only the third depth 250'" deeper than the second depth are provided. By providing different sized slots in different regions, the thickness of the cylindrical wall 262, and the webs 264, are also varied in each of regions 266, 268 and 270, as is shown in FIGS. 6 to 12. FIGS. 6 and 7 show the slots 230, 232 of third region 270, FIGS. 9 and 10 show the slots 230, 232 of the second region 268 and FIGS. 11 and 12 show the slots 230, 232 of the first region 266. FIG. 8 shows the section of a rib 260, showing that each of the ribs 260 has a generally equal outer circumference. Each region 266, 268 and 270 of slots is also provided along a discrete length of the rod 200. As a result, three region of different stiffness regions are provided, a first region 266 having the greatest depth slots 230, 232 and thus the lowest stiffness, the second region 268 having greater stiffness with slightly shallower slots 230, 232, and the third region 270 having the shallowest slots 230, 232. Additionally, to enhance the variation in stiffness, the thickness of the ribs 260 is the same in each region, but different between region. Thus, ribs 260 thinnest in the first region 266, greatest in the third (stiffest) region 270, and of intermediate thickness in the second region 268.

By providing a generally fixed outer perimeter or cross section, and a variable smaller circumference or cross section composed of generally evenly spaced slots of progressively deeper depth slots, a variation in stiffness is integrally provided by rod 200. The slots only marginally reduce the ability of the middle member to act as a diametral spacer. In the embodiment of the variable stiffness member shown in FIG. 5, the widest and deepest slots are disposed furthest from the stent stop, and thus the greatest flexibility, or lowest stiffness, is located on the portion of the rod 200 furthest from the stent stop and stent graft 12, by varying the location at which the greatest width and deepest depth slots are located, the relative location of the lowest stiffness portion may be changed. Additionally, the slot widths and depths may be grouped differently, such as by providing the deepest, widest slots at a position generally midway between ends 210, 212 and having slots of smaller width and depth to either side of the middle region. Alternatively, only the depth or the width of the slots 230, 232, or the width of the ribs 260 between the slots may be varied to provide the lower stiffness region. Further, the lowest stiffness region may be located adjacent to the stent stop, and the lowest stiffness region may be provided by having more than three distinct sets of slots of equal depth and width. For example, the each slot could have different widths and depths, so that a progressively more (or less stiff) region of the rod 200 would be created along the length of the rod 200.

Figure 5A:
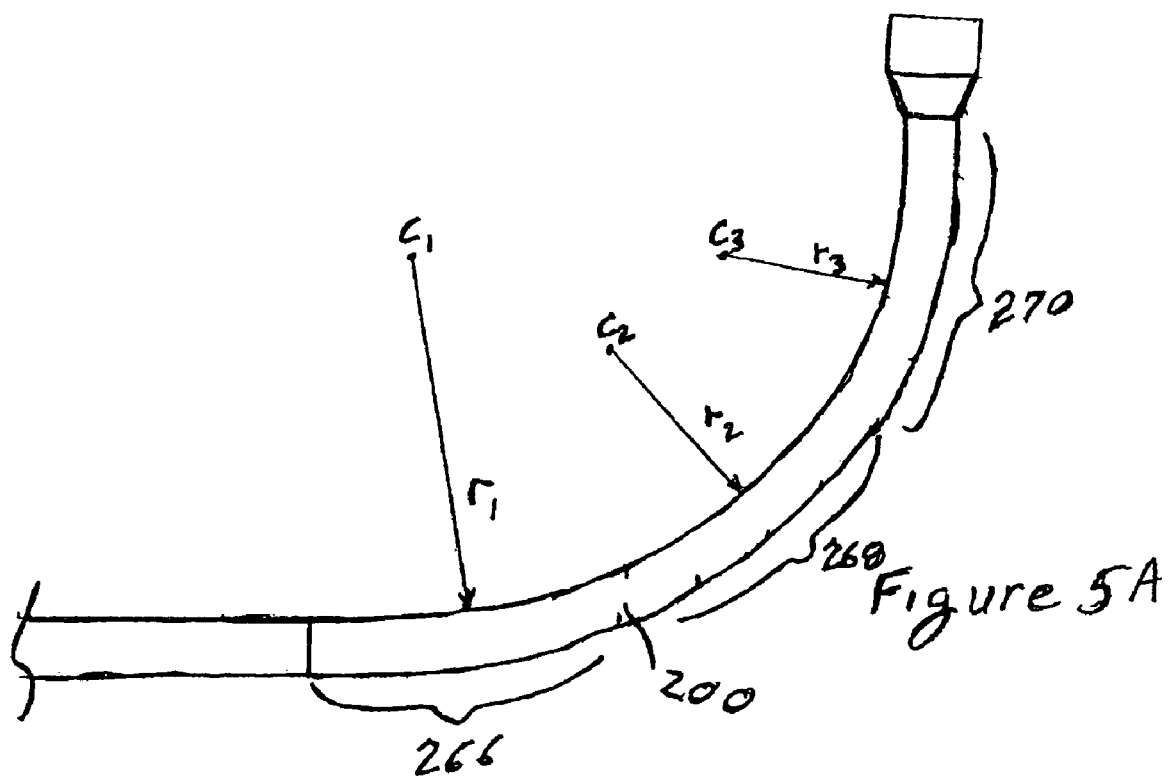
FIG. 5A is a side view of the variable stiffness member of FIG. 5, showing the effect of bending forces thereon.

By providing different regions of stiffness along the length of the rod 200, the all portions of the rod 200 should bend when subjected to a bending moment from forces imposed to either side of the ends thereof. Referring to FIG. 5A, this is schematically demonstrated, wherein bending will be greatest in the least stiff portion 270 where the rod will curve along radius $r_3$ centered at $c_3$, and least in the first region 266 where the rod 200 curves along radius $r_1$ centered on $c_1$, with intermediate bending of middle portion 268 along $r_2$ centered at $c_2$, where $r_1$ is greater than $r_2$, and $r_2$ is greater than $r_3$. Thus, there is created on the rod 200 a continuous curve which will help distribute the bending load along the rod 200, and thus along the graft cover 227 (FIG. 5), to minimize the likelihood of buckling of the graft cover thereover, as well as provide a locating, proximal to the stent stop 214, where buckling if it is to occur, will preferentially occur in the graft cover 227.

Figure 14:
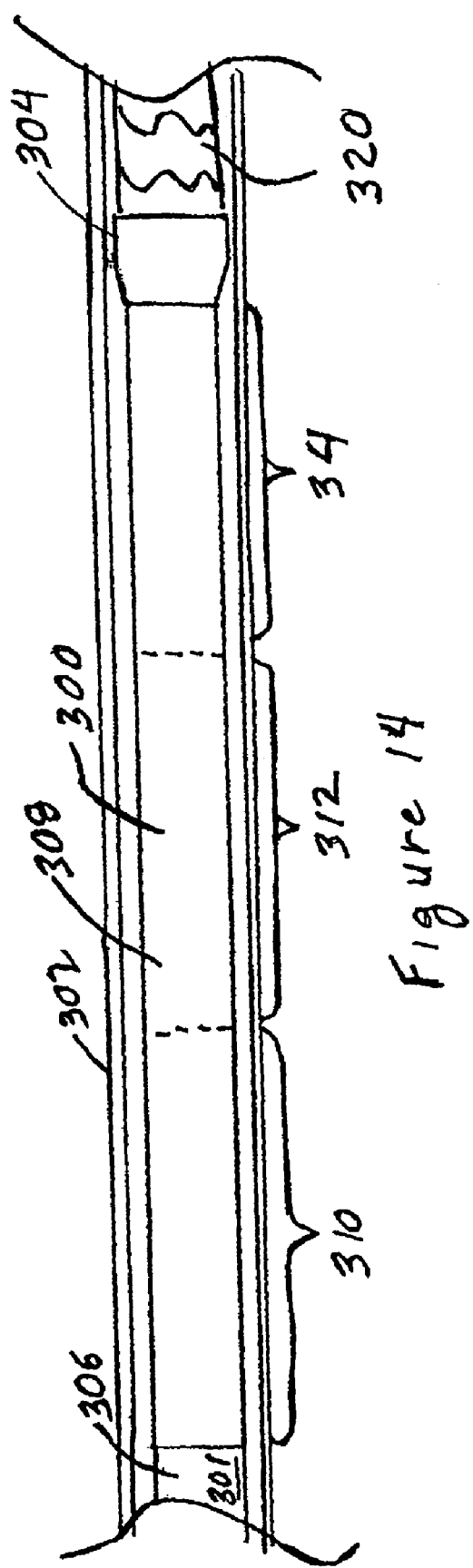
FIG. 14 is cross sectional view of an additional alternative embodiment of the variable stiffness member.

Referring now to FIG. 14, an additional embodiment of a variable flexible member is shown, wherein a portion of the middle member is modified to include a linear portion formed several portions (sub-portions) or sections, the material in each section having a different durometer to provide the variable flexible member. Specifically a variable durometer middle member 300 is provided, wherein a first portion 301 of the middle member extends, as in the embodiment described previously herein, distally from a position at the proximal end (not shown) of the delivery system, to a distal end 306 of uniformly constructed materials positioned adjacent to, but spaced from, a stent stop 304. Disposed in the space or gap between the distal end 306 of the first portion 300 and the stent stop 304 is disposed an extension portion 308 having three distinct sub-portions, or a first sub-portion 310, a second sub-portion 312 and a third sub-portion 314. Each of sub portions 310, 312 and 314, as well as the first portion 301 of middle member 300 are cylindrical lengths of Vestamid of Pebax material, having a length and a diameter, each length being substantially equal for each of the sub-portions 310, 312 and 314, and a diameter which is substantially equal to that of the first portion 301. Each of first, second and third sub-portions 310, 312 and 314 are affixed (by gluing or melting) to each other, end to end, such that first sub-portion 310 is affixed at one end thereof to the first portion 300 of the middle member, and at its other end to one end of the second sub-portion 312. Second sub-portion is likewise affixed, at its other end, to one end of the third sub-portion 314, which in turn is affixed, at its other end, to the stent stop 304. Each of the three sub-portions 310, 312 and 314 is provided from materials having a different durometer hardness than the adjacent sub-portion. For example, in one aspect first sub-portion 310 is provided from material having a hardness of 6333 Durometer A, second sub-portion 312 is provided from material having a hardness of 6033 Durometer A, and third sub-portion 314 is provided from material having a hardness of 5533 Durometer A, whereas the hardness of the first portion of middle member is 7233 Durometer A.

By providing sections or portions of the middle member of material having different hardnesses, a variable stiffness portion is provided. For a polymer such as Pebax or Vestamid, the greater or larger the durometer number, the greater the stiffness or resistance to bending, of a resultant cylindrical member configured of the material. Thus, as described, the greatest durometer portion of the middle member has a lowest resistance to bending, e.g. greatest stiffness, in the first sub-portion 310 disposed between the first portion 301 of the middle member 300 and the second sub-portion 312. Additionally, as with the embodiment shown and described with respect to FIGS. 5 to 13 hereof, the use of multiple sub-portions in the middle member, wherein each sub-portion includes a different hardness durometer, enables the generation of a continuously decreasing radius curve along the length of the variable stiffness portion. Each sub-portion 310, 312 and 314 of the middle member will inherently bend, preferentially to the stiffer first portion 301 and the stiffer stent graft 320 when the delivery system is confronted by bending forces between the portion of the graft cover overlying the stent graft and a force imposed on the graft cover to the proximal side of the sub-portions 310, 312 and 314 will result in bending in each of the sub-portions, though sub portion 314 will have the greatest curvature, as it is the least stiff. Thus, as the variable flexible portion has a lower stiffness or resistance to bending moments, as compared to the stent graft or the first portion of the middle member, if any buckling occurs in the graft cover 302, it will occur preferentially in the region or span of the graft cover 302 overlying the variable stiffness sub-portions 310, 312 and 314. Additionally, because each sub-portion 310, 312 and 314 will bend when a bending force is applied to the delivery system, the bending will occur continuously over a longer length of the graft cover than will occur with the coil based embodiments of FIG. 1 to 4. By extending the length over which the bending occurs, the likelihood of buckling is reduced, even in the variable flexible portion of the delivery system. Likewise, as the variable flexible portion has a lesser resistance to bending forces than have the stent graft or the first portion of the middle member, the bending of the graft cover will occur preferentially in the region of the graft cover disposed immediately proximal to the stent stop 304, and thus if buckling or restriction of the cross section of the graft cover is encountered, it is encountered in a location at which it will not interferingly engage against the stent stop 304 as the graft cover 302 is retracted.

Figure 15:
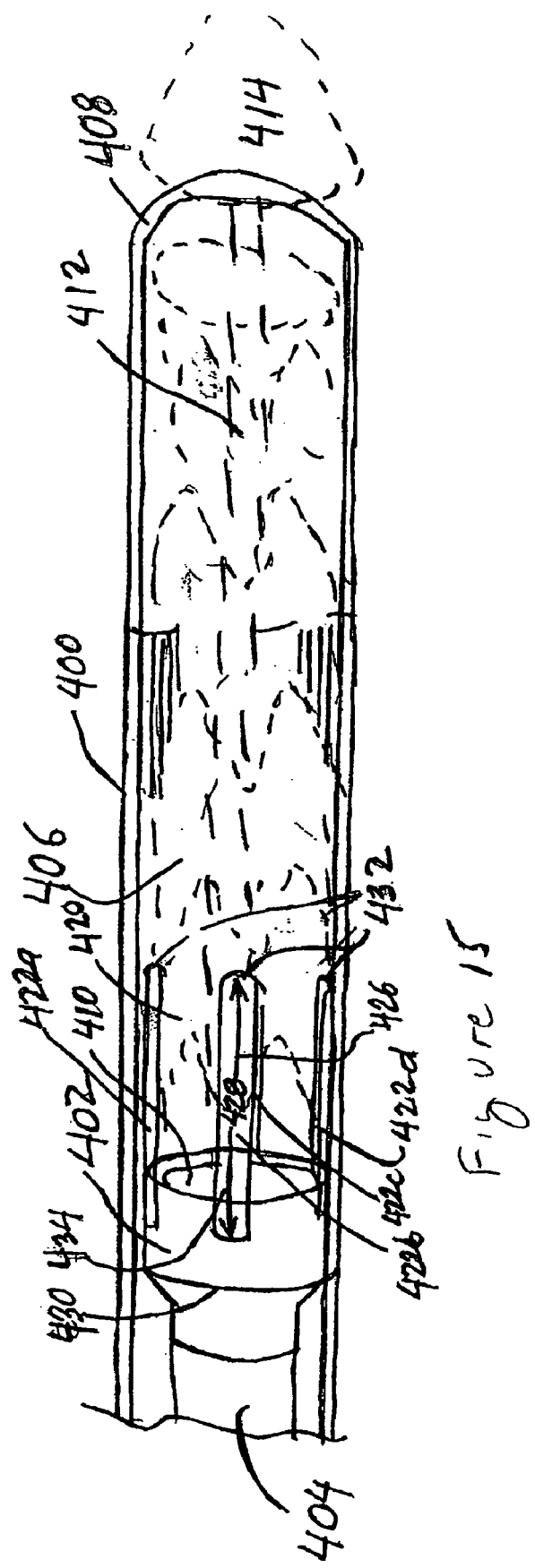
FIG. 15 is a cut away partial perspective view of a portion of the delivery system of FIG. 1, showing a further alternative delivery system configuration, including runners extending from the stent stop to extend partially over the stent graft held within the delivery system prior to deployment.

Referring now to FIG. 15, there is shown an additional aspect, wherein the delivery system is modified to include a buckle expansion member to expand the graft cover, over the stent stop, in the event a buckle is encountered in the graft cover in the region where the graft cover overlies the stent graft. Specifically, a graft cover 400 extends distal of a stent stop 402, which is provided near the distal end of a middle member 404, and further overlies a compressed stent graft 406 (shown in phantom) held in the region of the graft cover 400 extending between stent stop 402 and open end 408 of the graft cover 400. Stent stop 402 includes a front face 410 from which extends a guidewire inner member 412 (shown with dashed lines) which extends to the proximal surface of a tapered introduction portion 414 (shown win phantom). During the tracking of the stent graft over a guidewire, the tapered introduction portion 414 is maintained over the open end 408 of the graft cover 400, but is moved off the graft cover 400 open end 408 by pushing the guidewire inner member 412 forward to position the (by being glued or captured in a melted ring capturing the end) tapered introduction portion 414 forward of the open end 408 of the graft cover 400.

A buckle expansion member 420 is provided in this configuration as a plurality of petals or runners 422a-d, which are affixed to the stent stop 402 (by being glued or captured in a melted ring capturing the ends) and extend, from the stent stop 402, to a position intermediate of the span of a stent graft 424 compressed and held within the graft cover 400. Each of petals 422a-d form a cantilevered beam, and include a generally thin planar body 426 having a width on the order of 5% of the circumference of the stent stop 402, and a length 428 extending from approximately the rear surface 430 of the enlarged portion of the stent stop 402 to an end 432 located approximately one-third the length of the compressed stent graft 406 held in the graft cover 400. End 432 is rounded off, into a radius. Additionally, each of petals 422a-d include relatively weaker, in bending strength, portion 434 generally adjacent to the stent stop 402. This weaker portion may be formed by providing the petals 422a-d with a smaller thickness and or width at that location. This weaker portion 434 allows the petals 422a-d to bend inwardly if a buckle is passed over their ends 432, but have sufficient rigidity from theory end to the lower stiffness region 434 such that the buckle can be expanded when it reaches the stent stop 402, the petals 422a-d providing a bearing surface over which the buckle can slide and be passed or expanded over the stent stop 402. The petals are affixed to the stent stop 402 such as by the use of an adhesive. Petals 422a-d are preferably manufactured from a biocompatible stainless steel or from a biocompatible polymer.

Figure 18:
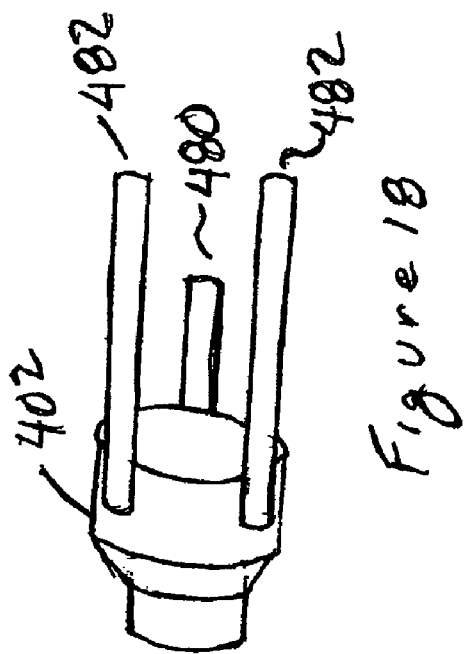
FIG. 18 shows yet another embodiment of a stent stop/runner configuration to that shown in FIG. 15.
Figure 16:
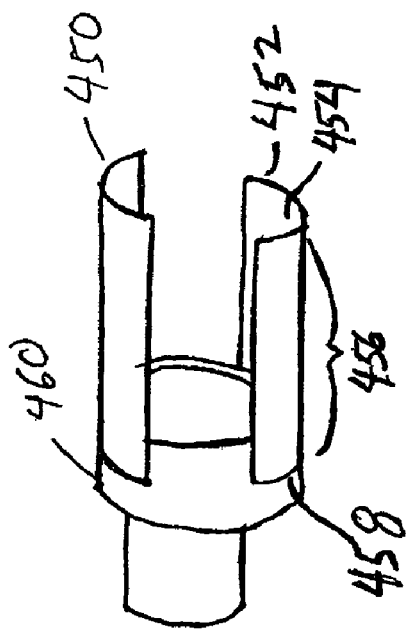
FIG. 16 shows an alternative stent stop/runner configuration to that shown in FIG. 15.
Figure 17:
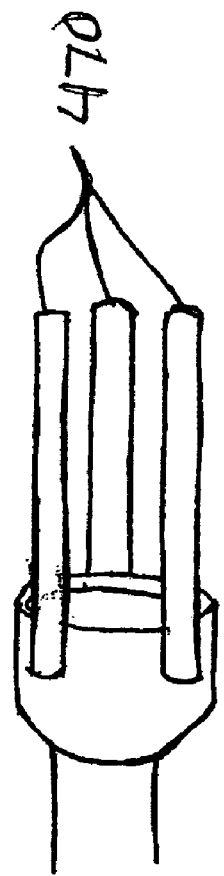
FIG. 17 shows another embodiment of a stent stop/runner configuration to that shown in FIG. 15.

Referring now to FIGS. 16 to 18, additional configurations of the petals are shown. In FIG. 16, two semi-cylindrical petals 450, 452 are provided. Each pedal is formed of a partial section of a cylinder, such that each of petals 450, 452 is defined as a partial circumference of a cylinder having an arcuate section 454 and a length 456 spanning a first end 458 affixed to the outer circumference 460 of stent stop 402, and a second end 462 spaced from the front face of the stent stop 402.

FIG. 17 shows an additional pedal configuration wherein three petals 470a-c are equally spaced about the circumference of the stent stop 402, each pedal having a configuration and function substantially similar to petals 422a-c shown and described with respect to FIG. 15.

FIG. 18 shows yet another configuration of petals or runners. In this configuration, three petals 480, 482 and 484 are provided, equally spaced about the circumference of the stent stop 402 and affixed at one end thereof to the outer circumferential surface of the stent stop 402. In this configuration, the petals have different lengths, i.e., they extend different distances from the stent stop, wherein petal 480 has a first length and 482, 484 each have an equal length which is greater than that of petal 480. Alternatively, two of the petals could be shorter, and the third one longer. Likewise, multiple petals, including more than three, all of different lengths or of groups of different lengths, may be provided.

Thus, there are shown and described, multiple configurations for decreasing the likelihood of encountering a condition, during the delivery and deployment of an exclusion device, whereby the graft cover will not retract over the middle member and stent stop, or might partially retract over the middle member and stent stop, thereby resulting in partial deployment of the exclusion device and a resulting need for immediate invasive surgical intervention.

We claim:

1. An apparatus for intravascular delivery of a device, comprising:
    a tubular portion, having a proximal end and a distal end, said tubular portion including a first receiving portion within which may be held a device to be intravascularly delivered and a second portion through which a manipulator may be provided; and
    a manipulator extendable along the second portion of said tubular portion, said manipulator having a uniform outer diameter and an inner diameter and including a first manipulator region extendable along the second region of said tubular portion, a second manipulator portion, having a different resistance to bending than said first portion of said manipulator, disposable adjacent to the first portion of said tubular portion and a third portion, having a different resistance to bending than that of said first portion and said second portion,
    each of said first region, said second region and said third region comprised of a plurality of opposed crescent shaped slots having a partial circumferential inner wall and co-planer bases on opposed sides of said partial circumferential inner wall, such that no slot extends into said inner diameter of said manipulator and a continuous inner diameter sleeve portion is provided over the length of said manipulator at least through said first, second and third regions and the slots of said first region have a substantially equal depth said slots in said second region have a different, substantially equal depth as compared to those in said first region and said slots in said third region have a substantially equal depth different than said slots in said first and second regions, such that each of said first region, said second region and said third regions have different resistances to bending the resistance to bending of each region being distinct from any other region, and uniform over the span of the slots in said region.

2. The apparatus of claim 1, wherein said co-planer bases of opposed slots form a rib.

3. The apparatus of claim 2, wherein said ribs in said first region and said ribs of said second region have different widths.

4. The apparatus of claim 3, wherein said partial circumferential wall in each of said slots has a thickness extending from said inner diameter and said slot, and said thickness of said partial circumferential wall in said first region is different than the thickness of said partial circumferential wall in said second region.

* * * * *